United States Patent
Chang et al.

(10) Patent No.: US 7,541,479 B1
(45) Date of Patent: Jun. 2, 2009

(54) DIRECT EPOXIDATION PROCESS

(75) Inventors: Te Chang, West Chester, PA (US); Arsam Behkish, King of Prussia, PA (US); Jude T. Ruszkay, Coatesville, PA (US); John H. Speidel, Jr., Media, PA (US); Patrick N. Crowe, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 0 days.

(21) Appl. No.: 12/154,730

(22) Filed: May 27, 2008

(51) Int. Cl.
*C07D 301/10* (2006.01)
(52) U.S. Cl. .................. 549/533; 549/532; 549/531
(58) Field of Classification Search ................ 549/533, 549/532, 531; 502/245, 66, 243
See application file for complete search history.

(56) References Cited

U.S. PATENT DOCUMENTS

| | | | |
|---|---|---|---|
| 4,954,325 A | 9/1990 | Rubin et al. | |
| 5,973,171 A | 10/1999 | Cochran et al. | |
| 6,077,498 A | 6/2000 | Diaz Cabañas et al. | |
| 6,114,551 A | 9/2000 | Levin et al. | |
| 6,376,686 B1 * | 4/2002 | Balan | 549/532 |
| 6,464,384 B2 * | 10/2002 | Kubera et al. | 366/102 |
| 7,138,535 B1 | 11/2006 | Whitman et al. | |
| 7,238,817 B1 | 7/2007 | Han | |
| 7,279,145 B2 | 10/2007 | Balan | |
| 2004/0124140 A1 * | 7/2004 | Sawyer et al. | 210/634 |
| 2007/0260075 A1 | 11/2007 | Jubin, Jr. et al. | |

FOREIGN PATENT DOCUMENTS

BE  1001038 A7  6/1989

OTHER PUBLICATIONS

Y. T. Shah et al., "Design parameters estimations for bubble column reactors" in AIChE Journal, (May 1982), pp. 353-379, vol. 28 (3).
R. Szostak, "Non-aluminosilicate molecular sieves" in Molecular sieves: Principles of synthesis and identification (1989), pp. 205-282, Van Nostrand Reinhold.
G. Vayssilov, "Structural and physicochemical features of titanium silicalites" in Catal., Rev.-Sci. Eng., (1997), pp. 209-251, vol. 39 (3).
T. Maschmeyer et al., "Heterogeneous catalysts obtained by grafting metallocene complexes onto mesoporous silica" in Nature, (Nov. 1995), p. 159, vol. 378 (9).
P. T. Tanev et al., "Titanium-containing mesoporous molecular sieves for catalytic oxidation of aromatic compounds" in Nature, (Mar. 1994), p. 321, vol. 368.
A, Corma et al., J. Chem. Soc., Chem. Commun., (1998), p. 579.
D. Wei et al., "Catalytic behavior of vanadium substituted mesoporous molecular sieves" in Catal. Today, (1999), pp. 501-511, vol. 51.

* cited by examiner

*Primary Examiner*—Bernard Dentz
*Assistant Examiner*—David E Gallis
(74) *Attorney, Agent, or Firm*—Yuanzhang Han

(57) ABSTRACT

A process is disclosed for reacting an olefin, hydrogen, and oxygen in a slurry comprising a catalyst and a solvent in a reactor having a column and at least one side arm. The column is operated in a churn-turbulent flow regime. The slurry is circulated through the side arm, filtered, and exits the reactor.

15 Claims, 1 Drawing Sheet

DIRECT EPOXIDATION PROCESS

FIELD OF THE INVENTION

The present invention relates to a process for epoxidizing an olefin in a slurry bubble-column reactor. Epoxide is produced by reacting an olefin, oxygen, and hydrogen in a solvent in the presence of a catalyst.

BACKGROUND OF THE INVENTION

A slurry bubble-column reactor is operated by suspending catalytic particles in liquid and feeding gas reactants into the bottom of the reactor through a gas distributor, which produces small gas bubbles. As the gas bubbles rise through the reactor, the reactants are absorbed into the liquid and diffuse to the catalyst where, depending on the catalyst system, they are typically converted to gaseous and liquid products. The gaseous products are recovered from the top of the reactor. Liquid products are recovered from the suspending liquid by using different techniques like filtration, settling, hydrocyclones, magnetic techniques, etc. See Y. T. Shah, et al., *AIChE Journal* 28(3) (1982) 353-79.

Epoxides such as propylene oxide are important industrial chemical intermediates. An epoxide can be produced by direct oxidation of an olefin with oxygen and hydrogen in the presence of a catalyst (U.S. Pat. Nos. 5,973,171; 7,138,535; 7,238,817; and 7,279,145).

Direct epoxidation of olefins with oxygen and hydrogen is highly exothermic. The reaction selectivity is highly sensitive to the reaction temperature. U.S. Pat. Appl. Pub. No. 20070260075 teaches a tower reactor having a plurality of separate reaction zones wherein the reactant gases are reacted in a slurry of catalyst particles in a solvent. Heat removal zones are provided between the reaction zones. The reactor is suitable for propylene oxide production by reacting propylene, oxygen, and hydrogen in a liquid medium comprising a slurry of catalyst particles in a solvent such as methanol or methanol and water. The copending application Ser. No. 12/079,760, filed on Mar. 28, 2008, teaches an epoxidation process comprising reacting an olefin, oxygen, and hydrogen in a slurry comprising a catalyst and a solvent in a reactor to produce an epoxide, wherein the reactor is operated in a churn-turbulent flow regime.

SUMMARY OF THE INVENTION

The invention is a process for making epoxide from an olefin. It comprises reacting an olefin, oxygen, and hydrogen in the presence of a slurry comprising a catalyst and a solvent in a reactor having a column and at least one side arm, wherein the column is operated in a churn-turbulent flow regime. The slurry is continuously circulated through the side arm(s). The slurry is filtered in the side arm(s) to produce a filtrate comprising epoxide.

DETAILED DESCRIPTION OF THE INVENTION

Figure 1:
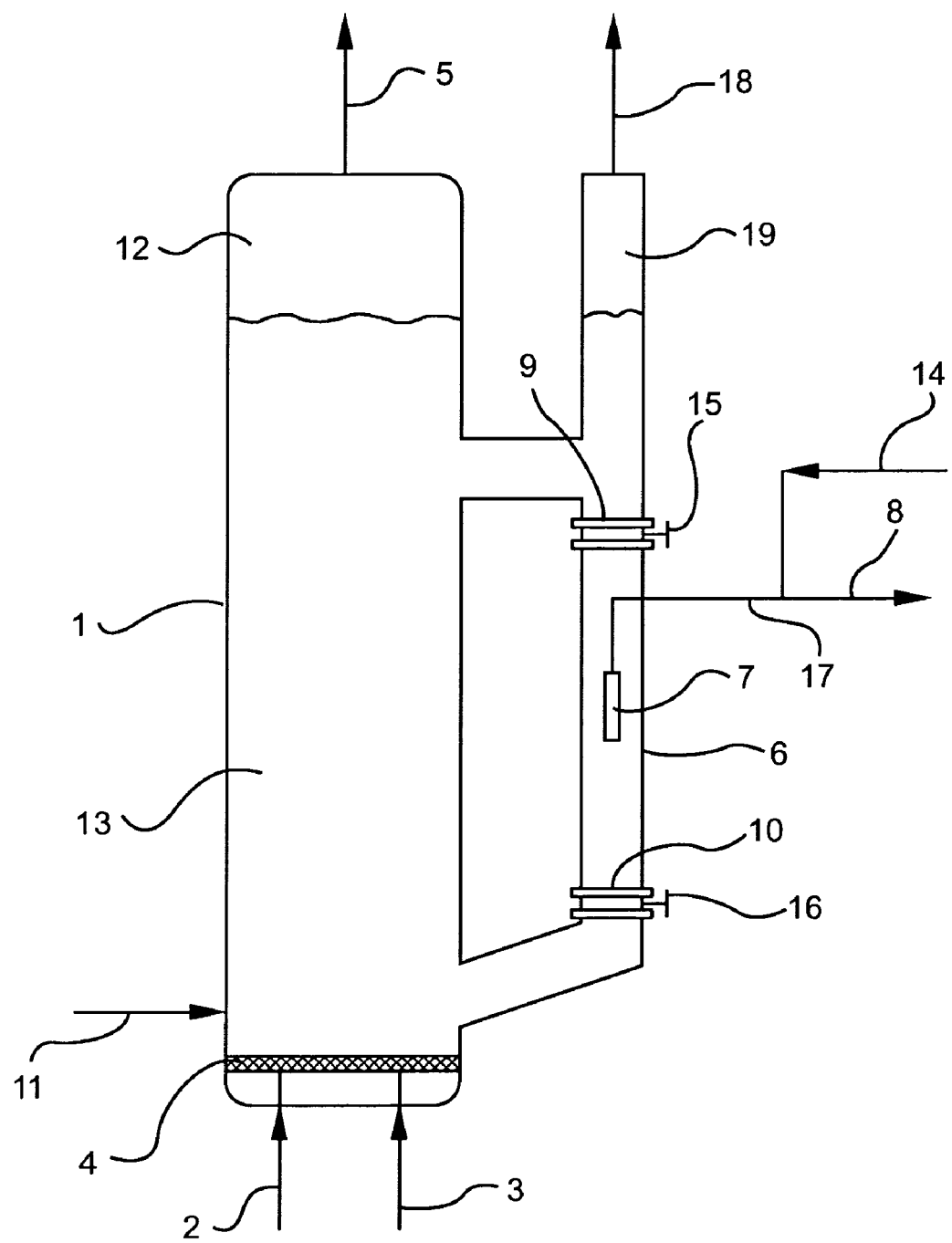
FIG. 1 is a schematic presentation of one embodiment of the present disclosure.

The process employs a catalyst. Suitable catalyst comprises a transition metal zeolite and a noble metal. Zeolites generally contain one or more of Si, Ge, Al, B, P, or the like, in addition to oxygen. A transition metal zeolite (e.g., titanium zeolite, vanadium zeolite) is a crystalline material having a porous molecular sieve structure and containing a transition metal. A transition metal is a Group 3-12 element. The first row of these includes elements from Sc to Zn. Preferred transition metals are Ti, V, Mn, Fe, Co, Cr, Zr, Nb, Mo, and W. Particularly preferred are Ti, V, Mo, and W. Most preferred is Ti. The type of transition metal zeolite employed depends upon a number of factors, including the size and shape of the olefin to be epoxidized. For example, it is especially advantageous to use titanium silicalite-1 (TS-1, a titanium silicalite having an MFI topology analogous to that of the ZSM-5 aluminosilicate) for the epoxidation of propylene. For a bulky olefin such as cyclohexene, larger pore zeolites may be preferred.

Suitable titanium zeolites include titanium silicates (titanosilicates). Preferably, they contain no element other than titanium, silicon, and oxygen in the lattice framework (see R. Szostak, "Non-aluminosilicate Molecular Sieves," in *Molecular Sieves: Principles of Synthesis and Identification* (1989), Van Nostrand Reinhold, pp. 205-282). Small amounts of impurities, e.g., boron, iron, aluminum, phosphorous, copper, and mixtures thereof, may be present in the lattice. The amount of impurities is preferably less than 0.5 weight percent (wt %), more preferably less than 0.1 wt %. Preferred titanium silicates will generally have a composition corresponding to the following empirical formula: $xTiO_2 \cdot (1-x)SiO_2$, where x is between 0.0001 and 0.5. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable. Particularly preferred titanium zeolites include the class of molecular sieves commonly known as titanium silicalites (see *Catal. Rev.-Sci. Eng.* 39(3) (1997) 209). Examples of these include TS-1, TS-2 (having an MEL topology analogous to that of the ZSM-11 aluminosilicate), and TS-3 (as described in Belgian Pat. No. 1,001,038). Titanium zeolites having framework structures isomorphous to zeolite beta, mordenite, ZSM-12, MCM-22, MCM-41, and MCM-48 are also suitable for use. Examples of MCM-22, MCM-41, and MCM-48 zeolites are described in U.S. Pat. Nos. 4,954,325, 6,077,498, and 6,114,551; Maschmeyer, T., et al, *Nature* 378(9) (1995) 159; Tanev, P. T., et al., *Nature* 368 (1994) 321; Corma, A., *J. Chem. Soc. Chem. Commun.* (1998) 579; Wei D., et al., *Catal. Today* 51 (1999) 501). The most preferred is TS-1.

Suitable noble metals include, e.g., gold, silver, platinum, palladium, iridium, ruthenium, rhenium, rhodium, osmium, and mixtures thereof. Preferred noble metals are Pd, Pt, Au, Re, Ag, and mixtures thereof. A catalyst comprising palladium is particularly preferred. Typically, the amount of noble metal present in the epoxidation catalyst will be in the range of from 0.01 to 20 wt %, preferably 0.1 to 5 wt %.

The noble metal and the transition metal zeolite may be on a single particle or on separate ones. For example, the noble metal may be supported on the transition metal zeolite. Alternatively, the catalyst may comprise a mixture of a transition metal zeolite and a noble metal supported on a carrier. Suitable carriers for the supported noble metal include carbons, titanias, zirconias, niobias, silicas, aluminas, silica-aluminas, titania-silicas, zirconia-silicas, niobia-silicas, ion-exchange resins, and the like, and mixtures thereof.

The manner in which the noble metal is incorporated into the catalyst is not critical. For example, the noble metal may be supported on the transition metal zeolite or other carriers by impregnation, ion exchange, adsorption, precipitation, or the like.

The weight ratio of the transition metal zeolite to noble metal is not particularly critical. However, a transition metal zeolite to noble metal ratio of from 10:1 to 10000:1 (grams of transition metal zeolite per gram of noble metal) is preferred.

The catalyst particles are generally very small in size and have a means mass diameter of 10-500 μm, preferably 20-100 μm. Catalyst particles of this size range can be produced by a number of means, one example of which is spray drying. Use of a catalyst of such size minimizes the mass transfer between the liquid and the catalyst due to large solid-liquid interfacial area. The concentration of the catalyst in the slurry is typically in the range of from 1 to 40 wt %, preferably in the range of from 5 to 30 wt %.

The process uses an olefin. Suitable olefins include any olefin having at least one carbon-carbon double bond and generally from 2 to 6 carbon atoms. Propylene is the most preferred. Any gas comprising propylene may be used. Typically, it comprises at least 90 wt % propylene. Preferably, it comprises greater than 95 wt % propylene.

The process uses oxygen. Any gas comprising oxygen may be used. Typically, it comprises at least 10 wt % oxygen. Preferably, it comprises greater than 90 wt % oxygen.

Similarly, the process uses hydrogen. Any gas comprising hydrogen may be used. Typically, it comprises at least 10 wt % hydrogen. Preferably, it comprises greater than 90 wt % hydrogen.

The molar ratio of hydrogen to oxygen can usually be varied in the range of $H_2:O_2$=1:100 to 10:1 and is especially favorable at 1:2 to 5:1. The molar ratio of oxygen to olefin is usually 1:1 to 1:20, and preferably 1:1.5 to 1:10.

In addition to olefin, oxygen, and hydrogen, a diluent gas may be used to avoid forming a flammable mixture among other reasons. Suitable diluent gases include nitrogen, helium, argon, carbon dioxide, and saturated hydrocarbons with 1-4 carbon atoms, e.g., methane, ethane, propane, and n-butane. Mixtures of these diluent gases can be used. The molar ratio of olefin to the diluent gas is usually in the range of 100:1 to 1:20 and especially 20:1 to 1:20.

The process uses a solvent. Suitable solvents are liquid under the reaction conditions. They include, for example, oxygen-containing hydrocarbons such as alcohols, aromatic and aliphatic solvents such as toluene and hexane, nitriles such as acetonitrile, and water. Suitable oxygenated solvents include alcohols, ethers, esters, ketones, water, and the like, and mixtures thereof. Preferred oxygenated solvents include water, methanol, ethanol, isopropanol, tert-butanol, and mixtures thereof.

The process may use a buffer. The buffer is employed in the reaction to inhibit the formation of glycols or glycol ethers during the epoxidation, and it can improve the reaction rate and selectivities. The buffer is typically added to the solvent to form a buffer solution, or the solvent and the buffer are added separately. Useful buffers include any suitable salts of oxyacids, the nature and proportions of which in the mixture are such that the pH of their solutions preferably ranges from 3 to 12, more preferably from 4 to 10, and most preferably from 5 to 9. Suitable salts of oxyacids contain an anion and a cation. The anion may include phosphate, carbonate, bicarbonate, sulfate, carboxylates (e.g., acetate), borate, hydroxide, silicate, aluminosilicate, or the like. The cation may include ammonium, alkylammonium (e.g., tetraalkylammoniums, pyridiniums), alkylphosphonium, alkali metal, and alkaline earth metal ions, or the like. Examples include $NH_4$, $NBu_4$, $NMe_4$, Li, Na, K, Cs, Mg, and Ca cations. The preferred buffer comprises an anion selected from the group consisting of phosphate, carbonate, bicarbonate, sulfate, hydroxide, and acetate; and a cation selected from the group consisting of ammonium, alkylammonium, alkylphosphonium, alkali metal, and alkaline earth metal ions. Buffers may preferably contain a combination of more than one suitable salt. Typically, the concentration of the buffer in the solvent is from 0.0001 M to 1 M, preferably from 0.0005 M to 0.3 M. The buffer may include ammonium hydroxide which can be formed by adding ammonia gas to the reaction system. For instance, one may use a pH=12-14 solution of ammonium hydroxide to balance the pH of the reaction system. More preferred buffers include alkali metal phosphates, ammonium phosphates, and ammonium hydroxide. The ammonium phosphates buffer is particularly preferred.

The process comprises reacting the olefin, oxygen, and hydrogen in a slurry comprising the catalyst and the solvent in a reactor having a column and at least one side arm, wherein the column is operated in a churn-turbulent flow regime. Typically three flow regimes have been identified in a slurry bubble column: homogeneous, heterogeneous (or churn-turbulent), and slug flow regime. See Y. T. Shah, et al., *AIChE Journal* 28(3) (1982) 353-79. The superficial gas velocity and the column diameter are the main variables that determine the flow regime of the slurry bubble-column reactors. The superficial gas velocity is the gas volumetric flow rate at the reaction conditions divided by the internal cross-section area of the column. The homogeneous flow regime occurs when the superficial gas velocity is relatively low (e.g., <0.05 meter per second, m/s) and is marked by a narrow bubble-size distribution, and bubbles are distributed relatively uniformly over the cross section of a reactor, a column, or other vessels. In this regime the mixing intensity and axial dispersion are low due to weak bubble-bubble interactions. As the superficial gas velocity increases the uniform distribution of gas bubbles vanishes, and a highly turbulent flow structure appears. This is called a heterogeneous flow regime, where large bubbles or agglomerates of bubbles form and travel upward at high velocity, mainly near the axis of the vessel. The heterogeneous regime is also dependent on the column diameter and occurs at a certain column diameters typically above 0.10 m depending on the operating conditions and physical properties of the three-phase system. At lower diameter (i.e., <0.10 m) and high superficial gas velocities (e.g., >0.05 m/s) slug flow regime prevails where large bubbles are stabilized by the column wall and take on the characteristic slug shape. In this regime the mixing and mass transfer are very poor. Consequently, for a three-phase operation in a slurry bubble column, the churn-turbulent flow regime is preferred if good mixing is beneficial to the operation. Due to high gas flow rate and mixing intensity, there is a significant bubble-bubble interaction that results in a high level of bubble coalescence and break-up. Similarly a bimodal bubble size distribution (large and small gas bubbles) is observed. This is referred to as the two-bubble class mode. The large gas bubbles rise fast in the center of the column in a plug-flow manner and are responsible for the mixing, dispersion and solid suspension, whereas the small gas bubbles with low rise velocity are entrained in the liquid backmixing and contribute mostly toward the enhancement of the gas hold-up and mass transfer. Furthermore, due to high liquid mixing in the churn-turbulent flow regime, most slurry bubble columns in this regime can operate at isothermal conditions.

In a slurry bubble column operated in a churn-turbulent flow regime, sufficient mixing is achieved without the use of a mechanical agitator. Elimination of a mechanical agitator reduces time and cost associated with the shut-down for the repair and maintenance of the agitator and necessary seals. It also frees up substantially more space within the reactor for heat transfer tubes, thus improving overall heat removal capability. Thus, the process gives improved operational and maintenance advantages.

Preferably the olefin, oxygen and hydrogen are fed to the column at or near its bottom. More preferably they are fed to the column via a gas sparger. The sparging of the gas bubbles is the main mechanism for mixing, catalyst suspension, and dispersion.

The column is preferably cylindrical in shape and has a diameter of at least 0.10 meter (m) and has a height-to-diameter ratio of at least 3:1. The column diameter has a significant effect on the flow regime of a slurry bubble column.

The reactor has at least one side arm. The side arm is attached to the column in an upright fashion at two locations of different heights to allow slurry circulation from the upper region of the column to the side arm and back into the lower region of the column. A filter is located within the side arm. Any appropriate filter may be used. Suitable filter types are sintered metals, woven fabrics, porous sheets, wedge wires, laminated metal meshes, nanofiber sheets, porous ceramics, and the like. An outlet line is attached to the filter for transferring filtrate separated from the slurry for downstream processing.

Preferably the reactor has two or more side arms attached to the column. Each side arm contains a filter so that maintenance of one filter may be performed while another filter is in service. The side arms are preferably detachable from the column. For example, the side arm may be attached to the column through flanges. Valves may be used to isolate the side arm so that the side arm may be removed from the column for maintenance.

A flow-control means is optionally installed in the side arm to adjust the circulation flow rate through the side arm. For example, a valve may be used for such purpose.

The process is typically performed at a temperature in the range of from 30 to 100° C., preferably in the range of from 50 to 70° C., and at a pressure of from 100 to 800 psig, preferably at 150 to 400 psig. A cooling coil is preferably used in the column to remove the heat of the reaction.

A vapor zone and a slurry zone are present in the reactor. A gaseous product stream is present in the vapor zone. The gaseous product stream in the reactor comprises the epoxide, olefin, hydrogen, oxygen, solvent vapor, and diluent gases if used. The gaseous product stream exits the reactor from the vapor zone. The epoxide may be isolated from the gaseous product stream by standard techniques. The remaining gases are preferably recycled to the reactor after the epoxide is separated. See copending application Ser. No. 12/079,760, filed on Mar. 28, 2008.

The process comprises continuously circulating the slurry from the column to the side arm and separating a filtrate from the slurry within the side arm. The slurry is filtered in the side arm to produce a filtrate, which comprises solvent, epoxide, dissolved gases, and buffer if used. The filtrate exits the side arm while the remaining slurry returns to the column. After the epoxide is removed from the filtrate, the remaining liquid is further processed for solvent recycle and/or byproduct removal. See copending application Ser. No. 12/079,760, filed on Mar. 28, 2008.

The driving force for the slurry recirculation is the hydrostatic head pressure differential between the column and the side arm caused by the difference in the gas holdup in these sections respectively. At steady state the energy input from the gas flow to the reactor is balanced by the energy dissipated in the column and the side arm to maintain the slurry recirculation. The superficial liquid velocity in the side arm is sufficient to prevent excessive cake build-up around the filter.

The superficial gas velocity in the column is preferably in the range of from 0.05 to 0.60 m/s. More preferably, it is in the range of from 0.08 to 0.20 m/s.

The ratio of the cross sectional area of the side arm to the column has a major effect on the hydrodynamic of the reactor. Generally, the ratio is in the range of from 0.04:1 to 0.5:1, preferably in the range of from 0.1:1 to 0.5:1.

It may be desirable to install heat-exchange devices to the side arm to control the temperature in the side arm. For example, heat-exchange tubes may be installed in the side arm. Alternatively, a jacketed side arm may be used.

As one embodiment of the present invention, a process for the epoxidation of propylene is illustrated in FIG. 1. The reactor is comprised of a column 1 and a side arm 6. The column has gas inlets 2 and 3 near the bottom and a gas outlet 5 at its top. A heat-exchanging tube (not shown) is installed in the column to remove the reaction heat. The side arm 6 is attached to the reactor through flanges 9 and 10. Valves 15 and 16 may be used to isolate the portion between the valves from the reactor so that the portion can be removed for maintenance.

A liquid feed is added to the reactor via line 11. The liquid feed may comprise a solvent, a buffer, and other recycled liquid streams from the process (e.g., recycled solvent). These components may be mixed outside the reactor and enter the column as a single feed stream, or they may be fed to the reactor through individual lines.

Gases are fed to the bottom of the column. A gas distribution apparatus 4 is used to distribute the gases to the cross section of the column to help the uniform mixing of the gases with the slurry in the column. The gases are dispersed to create small bubbles and distributed uniformly over the cross section of the column to maximize the intensity of mass transfer. Perforated plates and ring spargers are preferably used for gas distribution.

Fresh propylene and hydrogen, and optionally recycled gases from the process may be combined into one feed stream and fed to the column via line 3. Oxygen enters the column through a separate line 2 and sparger 4.

The slurry containing entrained gases enter the top of the side arm from the column. The slurry flows downward in the side arm and flushes the filter 7 continuously to prevent excessive cake build-up around the filter. The liquid product stream passes through the filter 7 and exits the side arm from line 8.

The gaseous product stream exits the reactor from line 5 at the top of the column. The side arm has a gas disengagement zone 19. Gases exit the side arm via line 18.

A solvent back-flush may be applied to the filter 7 through lines 14 and 17 to clean the filter.

When it is necessary to replace the filter, the side arm may be isolated by closing valves 15 and 16. If the reactor has two or more side arms, maintenance work may be performed to one filter in one side arm while a filter in another side arm is in service, eliminating the need to shut down the process.

We claim:

1. An epoxidation process comprising reacting an olefin, oxygen, and hydrogen in the presence of a slurry comprising a catalyst and a solvent in a reactor having a column and at least one side arm; circulating the slurry from the column to the side arm; and separating a filtrate comprising epoxide from the slurry within the side arm; wherein the column is operated in a churn-turbulent flow regime.

2. The process of claim 1 wherein the reactor has two or more side arms.

3. The process of claim 2 wherein at least one side arm is in service while another side arm is offline.

4. The process of claim 1 wherein the column is cylindrical and has a diameter of at least 0.10 meter and a height-to-diameter ratio of at least 3:1.

5. The process of claim 1 wherein the superficial gas velocity in the column is in the range of 0.05 to 0.60 meter per second.

6. The process of claim 1 wherein the superficial gas velocity in the column is in the range of 0.08 to 0.20 meter per second.

7. The process of claim 1 wherein the ratio of the cross sectional area of the side arm relative to the cross sectional area of the column is in the range of from 0.04:1 to 0.5:1.

8. The process of claim 1 wherein the ratio of the cross sectional area of the side arm relative to the cross sectional area of the column is in the range of from 0.1:1 to 0.5:1.

9. The process of claim 1 wherein the side arm has a flow-control means.

10. The process of claim 1 wherein reaction heat is removed from the side arm.

11. The process of claim 1 wherein the olefin, oxygen, and hydrogen are fed at or near the bottom of the column.

12. The process of claim 1 performed at a temperature in the range of 30 to 100° C.

13. The process of claim 1 performed at a pressure in the range of 150 to 400 psig.

14. The process of claim 1 wherein the catalyst comprises a transition metal zeolite and a noble metal.

15. The process of claim 1 wherein the olefin is propylene and the epoxide is propylene oxide.

* * * * *